(12) United States Patent
Frigoli et al.

(10) Patent No.: US 9,447,109 B2
(45) Date of Patent: Sep. 20, 2016

(54) CRYSTALLINE SALTS OF ASENAPINE

(75) Inventors: Samuele Frigoli, Garbagnate Milanese (IT); Davide Longoni, Rodano (IT); Tamara Danelli, Rodano (IT); Marco Alpegiani, Milan (IT)

(73) Assignee: OLON S.P.A., Rodano (IT)

( * ) Notice: Subject to any disclaimer, the term of this patent is extended or adjusted under 35 U.S.C. 154(b) by 224 days.

(21) Appl. No.: 14/113,091

(22) PCT Filed: Apr. 30, 2012

(86) PCT No.: PCT/IB2012/052151
§ 371 (c)(1),
(2), (4) Date: Oct. 24, 2013

(87) PCT Pub. No.: WO2012/150538
PCT Pub. Date: Nov. 8, 2012

(65) Prior Publication Data
US 2014/0051741 A1 Feb. 20, 2014

(30) Foreign Application Priority Data
May 2, 2011 (IT) ................................ MI2011A0734

(51) Int. Cl.
*C07D 491/044* (2006.01)
(52) U.S. Cl.
CPC ................. *C07D 491/044* (2013.01)
(58) Field of Classification Search
CPC ............ A61K 41/0057; A61K 31/40; C07D 487/22; C07D 487/04; C07D 519/00
USPC .......................................... 514/410; 548/421
See application file for complete search history.

(56) References Cited

U.S. PATENT DOCUMENTS

| 7,741,358 B2 * | 6/2010 | Heeres ................. C07D 491/04 514/410 |
| 7,750,167 B2 * | 7/2010 | Kemperman ........ C07D 207/08 548/416 |
| 2011/0046393 A1 | 2/2011 | Wang et al. |

FOREIGN PATENT DOCUMENTS

JP  EP 2166012 A1 * 3/2010 ........... C07D 313/14

OTHER PUBLICATIONS

C.W. Funke, et al., Physico-Chemical Properties and Stability . . . , Arzneim-Forsch./Drug Res., vol. 40, No. 5, 1990.
International Search Report issued in counterpart PCT Application No. PCT/IB2012/052151 on Sep. 17, 2012.
Written Opinion of International Searching Authority issued in counterpart PCT Application No. PCT/IB2012/052151 on Sep. 17, 2012.

* cited by examiner

*Primary Examiner* — Alicia L Otton
*Assistant Examiner* — Sagar Patel
(74) *Attorney, Agent, or Firm* — Silvia Salvadori, PC.; Silvia Salvadori

(57) ABSTRACT

Disclosed is asenapine phosphate of formula (I) and its enantiomer (I) which can be used to prepare asenapine maleate. Further disclosed is a monoclinic crystalline form of asenapine maleate.

(I)

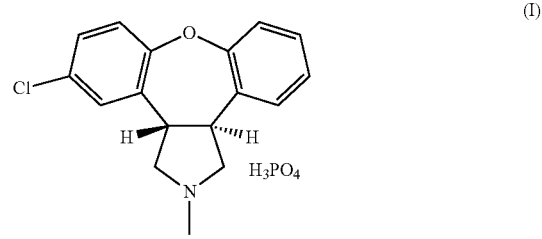

9 Claims, 14 Drawing Sheets

1044/09 – novel monoclinic form

106018 – monoclinic form of US7741358

106018 – monoclinic form of US7741358

106018 – monoclinic form of US7741358

1060/19 – orthorhombic form of US7741358

CRYSTALLINE SALTS OF ASENAPINE

This application is a U.S. national stage of PCT/IB2012/052151 filed on Apr. 30, 2012, which claims priority to and the benefit of Italian Application No. MI2011A000734 filed on May 2, 2011, the contents of which are incorporated herein by reference in their entirety.

SUMMARY OF THE INVENTION

The object of the invention is the novel crystalline salt asenapine phosphate, a process for its preparation, and its use to prepare asenapine maleate. A further object of the invention is a novel monoclinic polymorphic form of asenapine maleate, a process for its preparation, and pharmaceutical compositions containing it.

PRIOR ART

Asenapine, the chemical name of which is (3aR,12bR)-rel-5-chloro-2,3,3a,12b-tetrahydro-2-methyl-1H-dibenz[2,3:6,7]oxepino[4,5-c]pyrrole, is a compound with antipsychotic activity developed, in the form of a salt with maleic acid (Org 5222), for the treatment of schizophrenia and episodes of mania. The pharmacological profile of asenapine maleate and the first efficacy studies on patients were described in the literature in the early 1990s [Arzneim.-Forsch. 40, 540-554 (1990); Drugs of the Future 18, 1117 (1993)]; its chemico-physical characteristics are reported in detail in the publication Arzneim.-Forsch. 40, 536-539 (1990).

The class of tetracyclic compounds to which asenapine belongs was claimed, and its preparation disclosed, in BE 854915 and U.S. Pat. No. 4,145,434. Various improved processes for the preparation of asenapine (U.S. Pat. No. 7,872,147, U.S. Pat. No. 7,750,167, U.S. Pat. No. 7,875,729) and crystalline forms of asenapine maleate (U.S. Pat. No. 7,741,358, US 2008090892) were subsequently described.

U.S. Pat. No. 4,145,434 refers generically to acid addition salts of tetracyclic amines, and the experimental part almost exclusively discloses the preparation of maleates. WO98/54186 claims asenapine salts with arylsulphonic acids, in particular benzenesulphonic acid, and the characteristics of said salts for use as medicaments per se. The same document lists a series of asenapine salts with carboxylic acids, only some of which (maleate, fumarate, pamoate and hemipamoate) can be isolated as solids, and only maleate and fumarate in crystalline form.

Asenapine pamoate and hemipamoate are disclosed in EP 569096, which claims the potential use thereof in depot pharmaceutical preparations. The same document also discloses a stable crystalline form of asenapine hemipamoate.

U.S. Pat. No. 7,750,167 discloses the purification of crude asenapine via hydrobromide, reconversion to asenapine base (ie. not salified), and final precipitation as maleate. However, the yields are rather low.

Asenapine base is described as an oil; it is therefore not purifiable by crystallisation, and often obtained with a low degree of purity, as described in U.S. Pat. No. 7,964,739 and U.S. Pat. No. 7,750,167.

Thus finding an efficient method for the purification of asenapine which is applicable on an industrial scale is of the greatest interest.

The experiments conducted by the Applicant led to the isolation of various asenapine salts, including the hydrochloride, sulphate and phosphate, and the isolation of a novel monoclinic crystalline form of asenapine maleate. It has now surprisingly been found that the salt with phosphoric acid is obtained with a high degree of purity and high yields. The novel monoclinic form of asenapine maleate possesses advantageous properties compared with the monoclinic form previously described.

DESCRIPTION OF THE INVENTION

Figure 1:
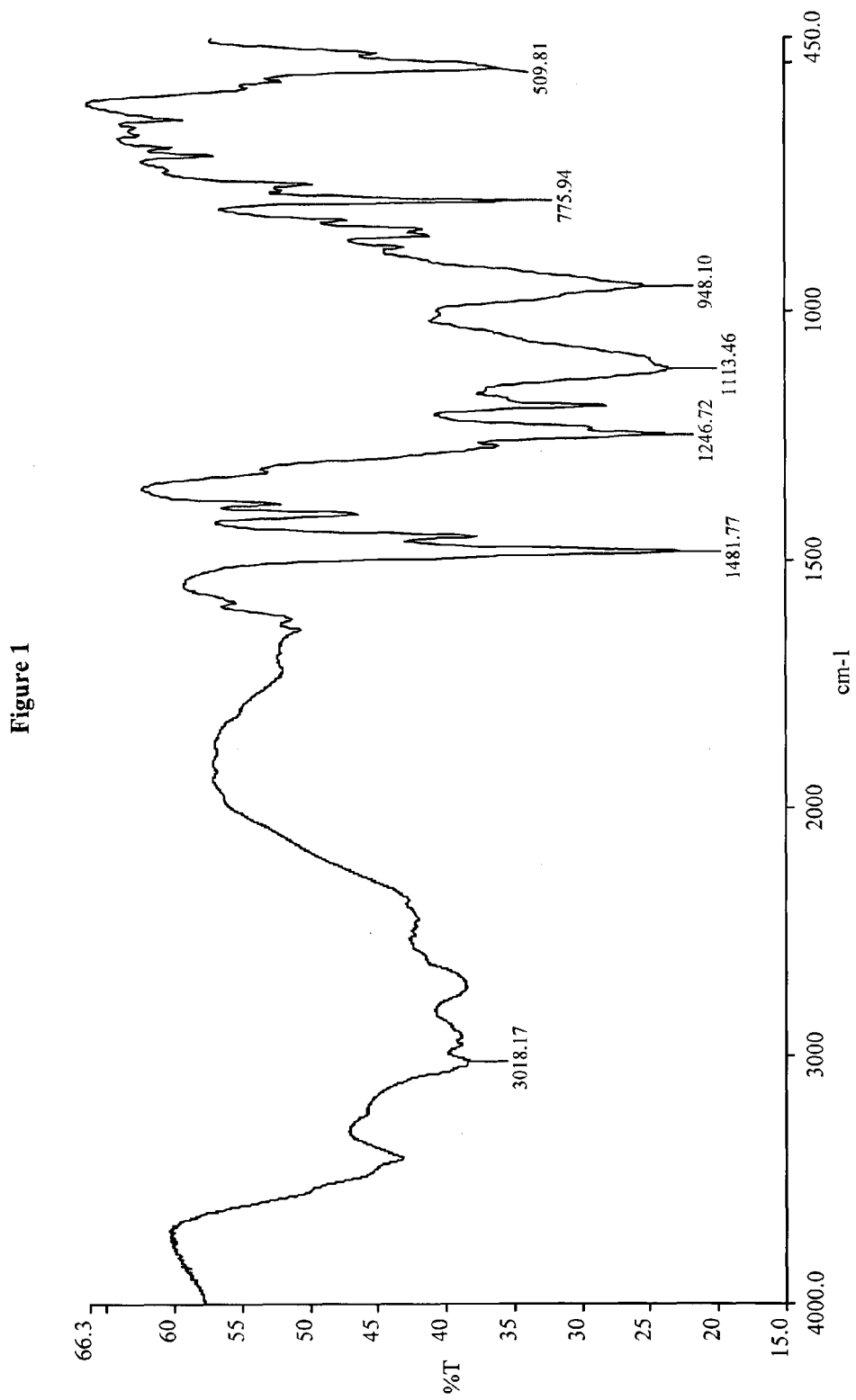
FIG. 1 shows the IR spectrum of asenapine phosphate.

The object of the present invention is asenapine phosphate of formula (I)

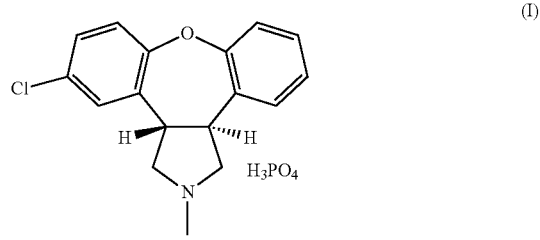

(I)

and its enantiomer.

The asenapine phosphate of the invention has a series of advantageous characteristics which make it particularly suitable for use in industrial processes to obtain asenapine maleate with high purity. In particular, the product is characterised by crystallinity, high HPLC purity (exceeding 99.5%), excellent filterability, stability in air and during storage, and is obtained in high yields.

The asenapine phosphate according to the invention is obtained from a solution of crude asenapine in an organic solvent by treatment with phosphoric acid.

Alternatively, the asenapine phosphate of the invention is obtained from an asenapine salt, which is converted to asenapine base by neutralisation of the salt. It is therefore a solution in organic solvent of the asenapine base thus obtained which upon treatment with phosphoric acid gives asenapine phosphate.

Both the processes disclosed above are a further object of the invention.

For both processes according to the invention, the solvents for the preparation of asenapine base solution are selected from ketones, such as acetone, methyl ethyl ketone, methyl iso-butylketone and cyclohexanone; esters or carbonates, such as ethyl acetate, butyl acetate, isopropyl acetate and dimethyl carbonate; ethers, such as tetrahydrofuran, methyl tetrahydrofuran, tert-butyl methyl ether, ethyl ether, di-isopropyl ether, diethoxymethane and ethylene glycol dimethyl ether; hydrocarbons, such as toluene, xylene, chlorobenzene, methylene chloride and chlorobutane; alcohols, such as methanol, ethanol, isopropanol and n-propanol; or mixtures of said solvents.

The solvents, or mixtures thereof, can contain variable percentages of water, up to 10%. The preferred solvents are alcohols, in particular ethanol, aqueous ethanol and isopropanol.

When the starting product for the preparation of asenapine phosphate is an asenapine salt, the aqueous solution of an inorganic base such as a bicarbonate, carbonate or hydroxide of alkaline or alkaline-earth metal, preferably an aqueous solution of sodium or potassium bicarbonate, carbonate or hydroxide, is used to release the asenapine base from its salt.

In both the processes according to the invention, if considered necessary, the solution of asenapine in organic solvent can be treated with a decolourising carbon or alumina (for example in batches under stirring for 5-30 minutes) and then filtered, or passed through a specific cartridge containing decolourising carbon or alumina, or passed through reverse-phase silica or adsorbent resin and then eluted.

The phosphoric acid can be used in anhydrous or hydrated form, or in aqueous, alcohol or water-alcohol solution. 1 to 2 moles of phosphoric acid per mole of asenapine are used, preferably 1.0 to 1.3.

The salification reaction of asenapine base with phosphoric acid can be conducted from ambient temperature to boiling point of the solvent or mixture of solvents.

The addition of phosphoric acid or a solution thereof can be performed instantly, or gradually over 1 hour, maintaining the reaction mixture under stirring.

Asenapine phosphate crystallises directly from the salification conditions or by cooling of the reaction mixture. The preferred crystallisation temperature is between 50° C. and −10° C. It can be advantageous to trigger crystallisation by adding a crystalline germ of asenapine phosphate, obtained by spontaneous crystallisation in earlier preparations conducted under the same experimental conditions according to the invention.

The asenapine phosphate crystals that separate from the reaction mixture are isolated by filtration and washed with a solution of a similar or identical composition to that of the mixture used to dissolve the asenapine base.

The product can be dried in a static or rotary drier, at 20-60° C. under vacuum.

The asenapine phosphate according to the invention has been characterised by IR, DSC and XRPD techniques.

FIG. 1 shows the IR spectrum of asenapine phosphate, which presents peaks at wavenumbers of approx. 3018 $cm^{-1}$, 1481 $cm^{-1}$, 1247 $cm^{-1}$, 1113 $cm^{-1}$, 948 $cm^{-1}$, 776 $cm^{-1}$ and 510 $cm^{-1}$.

A wavenumber value as indicated above typically signifies the specified value±2 $cm^{-1}$.

Figure 2:
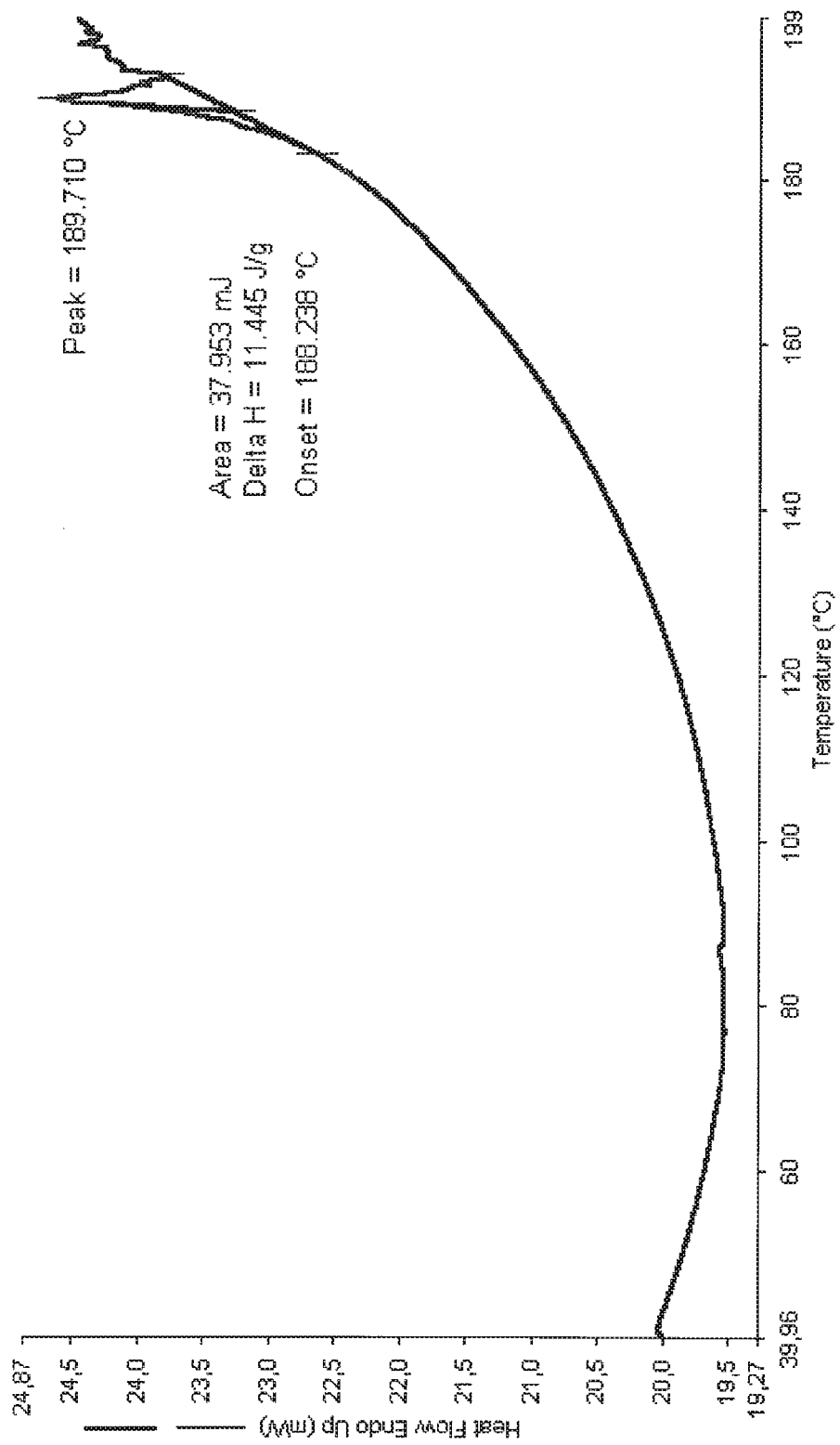
FIG. 2 shows the DSC thermogram of asenapine phosphate.

FIG. 2 shows the DSC thermogram of asenapine phosphate, which indicates a melting point (peak) of approx. 190° C.

Figure 3:
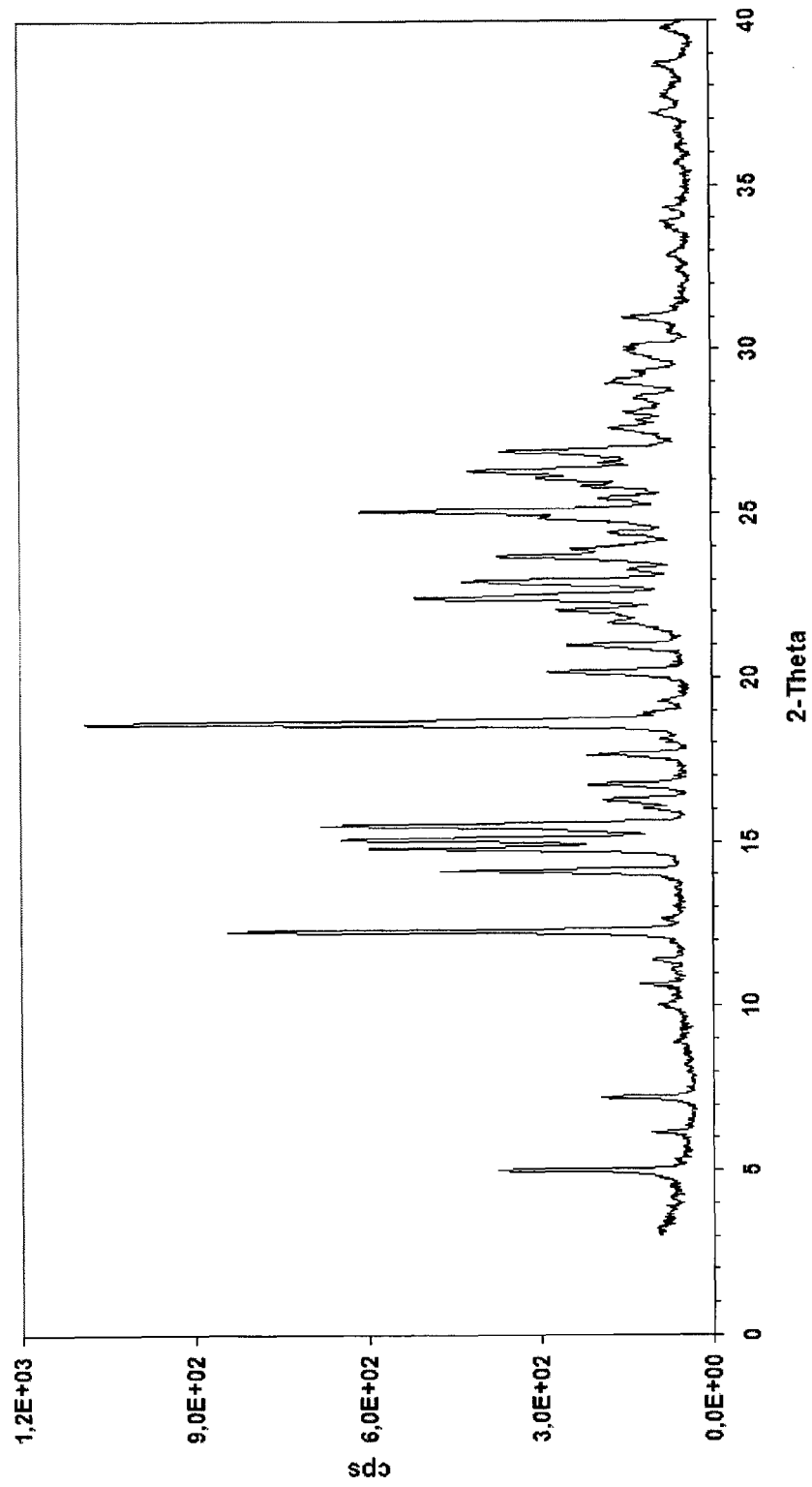
FIG. 3 shows the XRPD spectrum of asenapine phosphate.

Asenapine phosphate is characterised by the XRPD spectrum shown in FIG. 3. The X-ray diffraction patterns were measured on an Ital Structures θ/θ automated diffractometer with CuKα radiation.

The 2θ angles, the interplanar distance and the intensity of the peaks are shown in Table 1. The most intense peaks are those at 2θ values of 12.32°; 14.14°; 14.82°; 15.10°; 15.54°; 18.66°; 22.44°; and 24.10°.

A 2θ value as indicated above typically signifies the specified value±0.2°.

TABLE 1

XRPD data for asenapine phosphate

| 2-theta angle (°) | Interplanar distance d (Å) | Intensity (%) |
|---|---|---|
| 5.02 | 17.5892 | 33 |
| 6.18 | 14.2900 | 10 |
| 7.24 | 12.2001 | 18 |
| 8.92 | 9.9057 | 6 |
| 10.06 | 8.7856 | 9 |
| 10.68 | 8.2769 | 12 |
| 11.42 | 7.7422 | 10 |
| 12.32 | 7.1786 | 77 |
| 13.10 | 6.7528 | 6 |
| 14.14 | 6.2584 | 42 |
| 14.82 | 5.9728 | 54 |
| 15.10 | 5.8626 | 56 |
| 15.54 | 5.6976 | 62 |
| 16.04 | 5.5211 | 11 |
| 16.30 | 5.4336 | 17 |
| 16.76 | 5.2855 | 19 |
| 17.68 | 5.0125 | 20 |
| 18.18 | 4.8757 | 8 |
| 18.66 | 4.7514 | 100 |
| 19.32 | 4.5905 | 9 |
| 20.20 | 4.3925 | 26 |
| 21.00 | 4.2269 | 23 |
| 21.72 | 4.0884 | 15 |
| 22.08 | 4.0226 | 25 |
| 22.44 | 3.9588 | 46 |
| 22.96 | 3.8703 | 39 |
| 23.32 | 3.8114 | 13 |
| 23.72 | 3.7480 | 34 |
| 23.94 | 3.7141 | 22 |
| 24.42 | 3.6422 | 15 |
| 24.88 | 3.5758 | 26 |
| 25.10 | 3.5450 | 56 |
| 25.48 | 3.4930 | 18 |
| 25.86 | 3.4425 | 21 |
| 26.10 | 3.4114 | 28 |
| 26.32 | 3.3834 | 39 |
| 26.58 | 3.3509 | 18 |
| 26.92 | 3.3093 | 34 |
| 27.62 | 3.2270 | 16 |
| 27.86 | 3.1998 | 12 |
| 28.10 | 3.1730 | 14 |
| 28.54 | 3.1250 | 12 |
| 29.00 | 3.0765 | 17 |
| 29.10 | 3.0662 | 15 |
| 29.36 | 3.0396 | 13 |
| 29.96 | 2.9801 | 13 |
| 30.10 | 2.9665 | 14 |
| 31.00 | 2.8824 | 14 |

TABLE 1-continued

XRPD data for asenapine phosphate

| 2-theta angle (°) | Interplanar distance d (Å) | Intensity (%) |
|---|---|---|
| 32.90 | 2.7202 | 7 |
| 33.74 | 2.6544 | 7 |
| 33.92 | 2.6407 | 8 |
| 34.34 | 2.6093 | 7 |
| 37.18 | 2.4163 | 8 |
| 38.64 | 2.3283 | 9 |
| 39.80 | 2.2631 | 8 |

The isolation of asenapine as asenapine phosphate can be used to improve the quality of asenapine maleate. The asenapine phosphate according to the invention can be converted to asenapine base by neutralisation with an organic or inorganic base as described above. The asenapine base is then converted to asenapine maleate according to known methods. A further object of the present invention is therefore a process for the preparation of asenapine maleate which comprises the conversion of asenapine or a salt thereof to asenapine phosphate by the processes according to the invention.

A further object of the present invention is a novel monoclinic polymorphic form of asenapine maleate, obtainable by treating a solution of asenapine base in an alcohol, preferably ethanol, methanol, isopropanol, n-propanol or mixtures thereof, with maleic acid or with a solution of maleic acid in an alcohol, characterised in that the crystallisation of asenapine maleate takes place by operating at a temperature of 0° C. to 60° C., preferably between 20° C. and 30° C. To facilitate the crystallisation of the product it may be appropriate to add a primer, represented by crystals of the novel monoclinic polymorphic form obtained by spontaneous crystallisation in earlier preparations conducted under the same experimental conditions.

The novel monoclinic form of asenapine maleate has been characterised by XRPD, IR and DSC techniques, which demonstrate that this novel polymorph differs from the orthorhombic and monoclinic polymorphs disclosed in U.S. Pat. No. 7,741,358.

Figure 4:
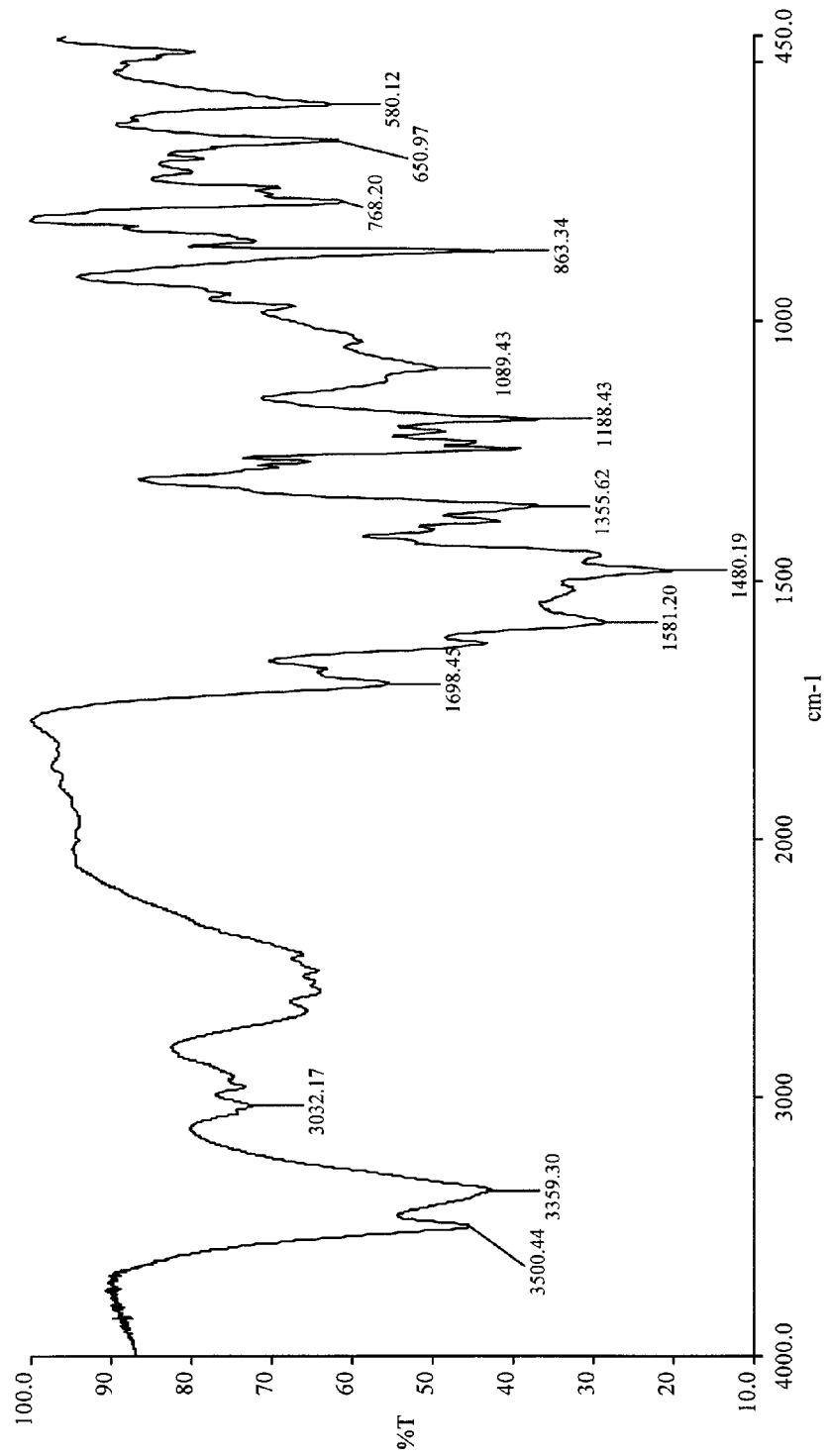
FIG. 4 shows the IR spectrum of the novel polymorphic form of asenapine maleate.

In particular, the infra-red spectrum of the novel polymorphic form of asenapine maleate is characterised by peaks with wavenumber values of approx. 3500 cm$^{-1}$, 3359 cm$^{-1}$, 3032 cm$^{-1}$, 1698 cm$^{-1}$, 1581 cm$^{-1}$, 1480 cm$^{-1}$, 1355 cm$^{-1}$, 1188 cm$^{-1}$, 1089 cm$^{-1}$, 863 cm$^{-1}$, 768 cm$^{-1}$, 651 cm$^{-1}$ and 580 cm$^{-1}$, as shown in FIG. 4.

Figure 7:
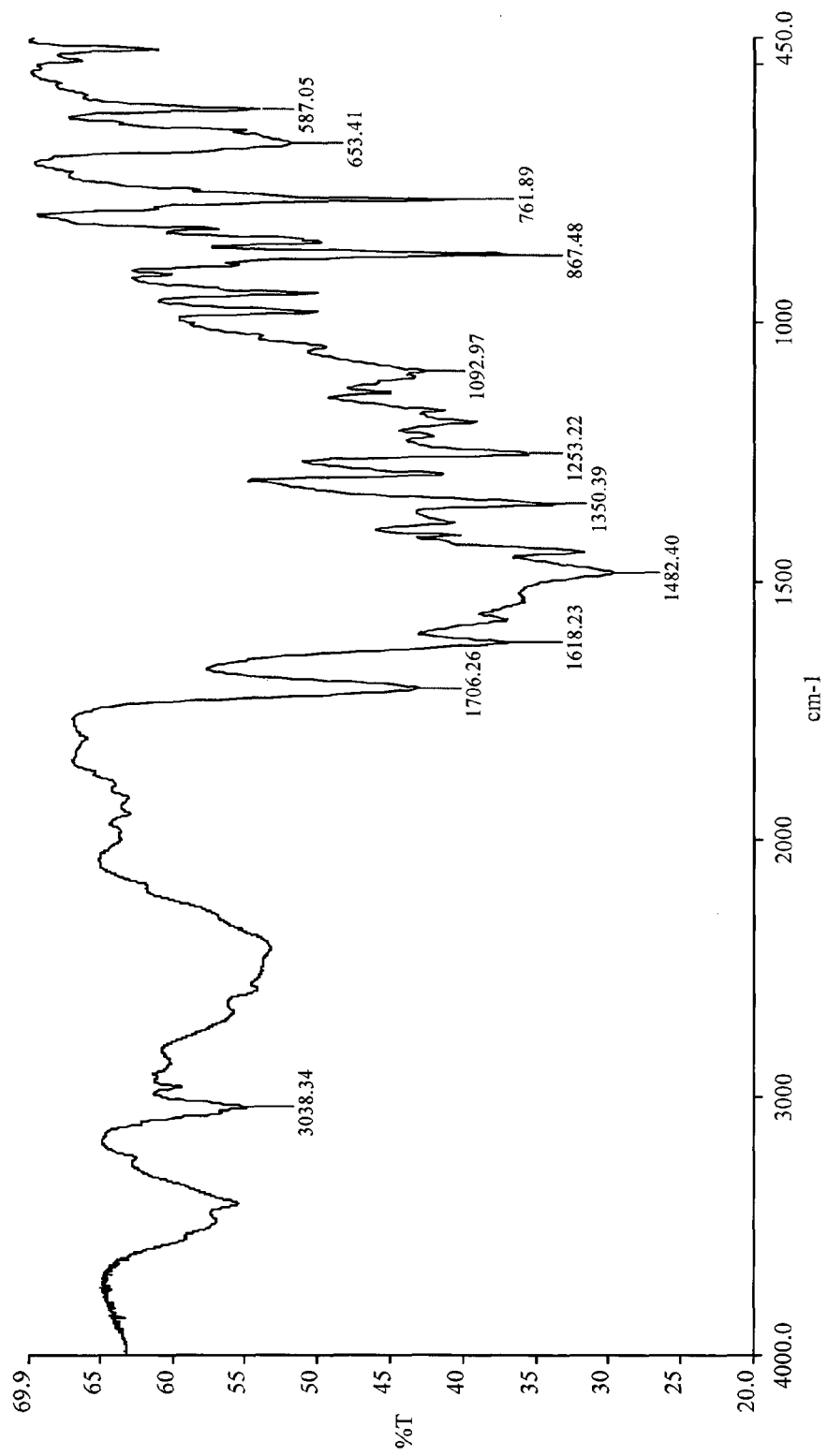
FIG. 7 shows the IR spectrum of the monoclinic form of asenapine maleate disclosed in U.S. Pat. No. 7,741,358.

The monoclinic form of asenapine maleate disclosed in U.S. Pat. No. 7,741,358 is characterised by an IR spectrum having peaks at wavenumber values of approx. 3038 cm$^{-1}$, 1706 cm$^{-1}$, 1618 cm$^{-1}$, 1482 cm$^{-1}$, 1350 cm$^{-1}$, 1253 cm$^{-1}$, 1093 cm$^{-1}$, 867 cm$^{-1}$, 762 cm$^{-1}$, 653 cm$^{-1}$ and 587 cm$^{-1}$, as shown in FIG. 7.

Figure 10:
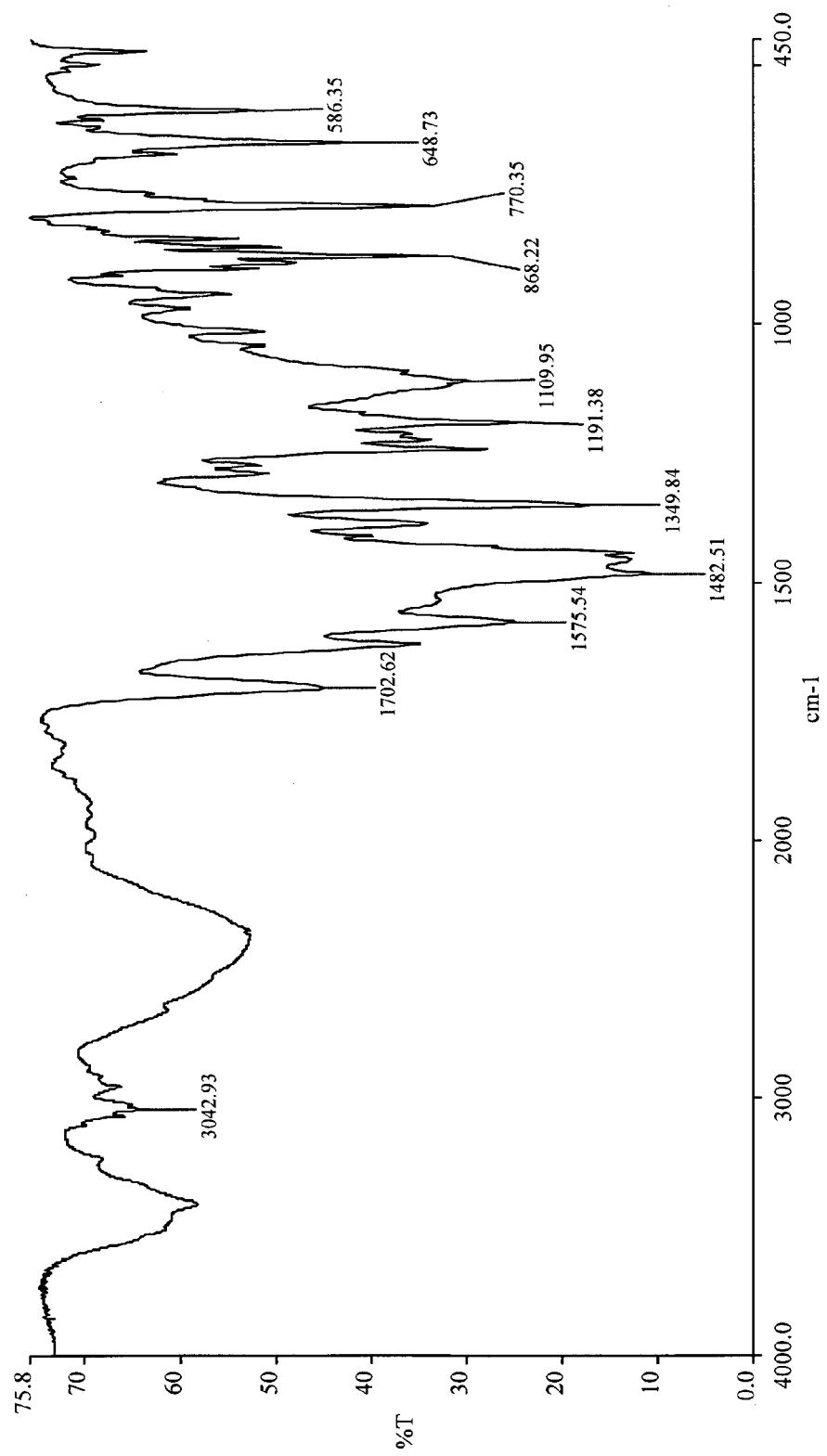
FIG. 10 shows the IR spectrum of the orthorhombic form of asenapine maleate disclosed in U.S. Pat. No. 7,741,358.

The orthorhombic form of asenapine maleate disclosed in U.S. Pat. No. 7,741,358 is characterised by an IR spectrum having peaks at wavenumber values of approx. 3043 cm$^{-1}$, 1703 cm$^{-1}$, 1576 cm$^{-1}$, 1483 cm$^{-1}$, 1350 cm$^{-1}$, 1191 cm$^{-1}$, 1110 cm$^{-1}$, 868 cm$^{-1}$, 770 cm$^{-1}$, 649 cm$^{-1}$ and 586 cm$^{-1}$, as shown in FIG. 10.

A wavenumber value as indicated above typically signifies the specified value±2 cm$^{-1}$.

Figure 5:
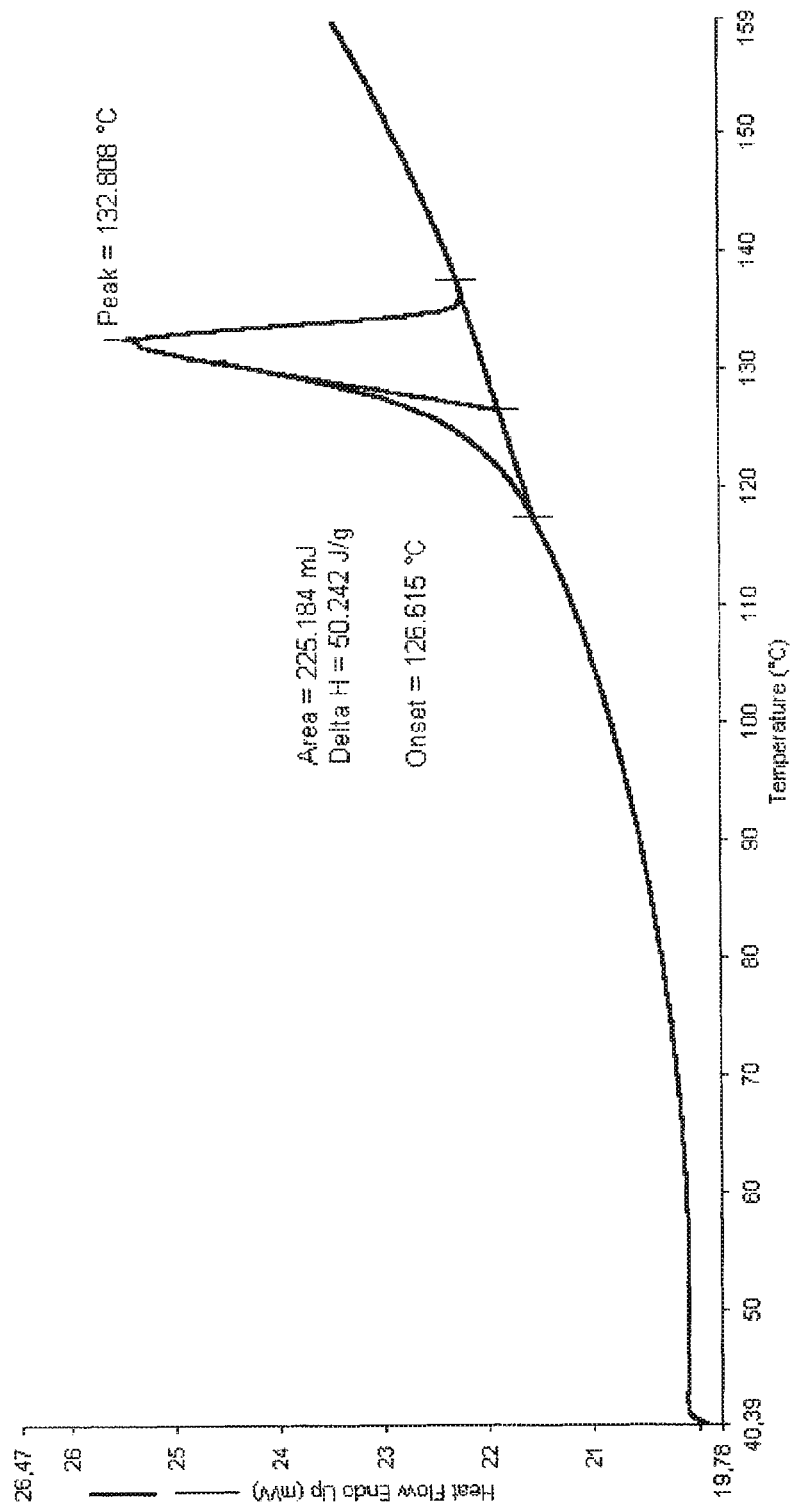
FIG. 5 shows the thermogram of the novel form of asenapine maleate.

The novel polymorphic form of asenapine maleate prepared according to the invention has a melting point (peak) of approx. 132.8° C., as demonstrated by the thermogram in FIG. 5, while the monoclinic and orthorhombic forms described in U.S. Pat. No. 7,741,358 have a melting point (peak) of approx. 147.2° C. and approx. 142.3° C. respectively, as indicated by the thermograms in FIGS. 7 and 11.

Figure 6:
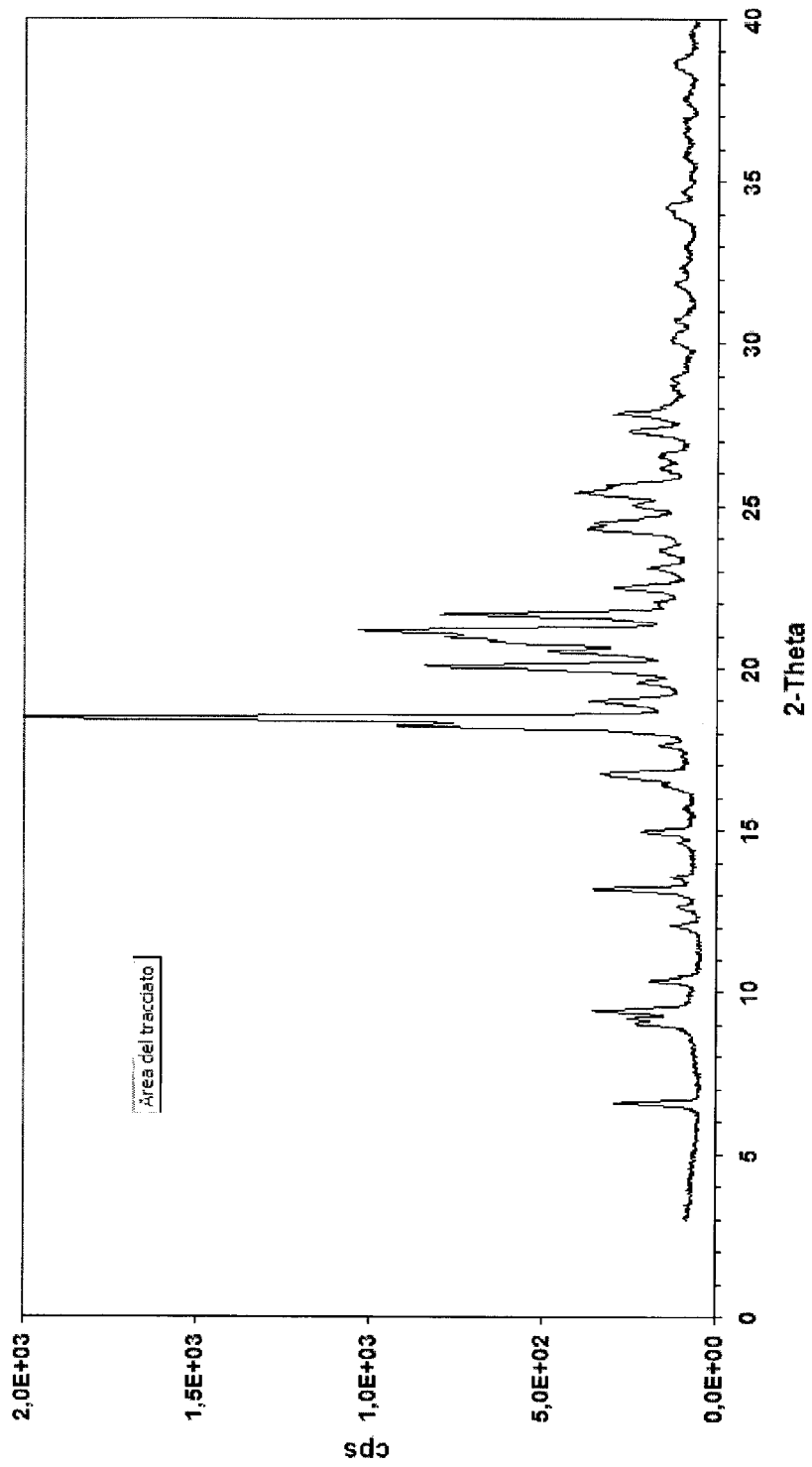
FIG. 6 shows the XRPD spectrum of the novel polymorphic form of asenapine maleate.

The novel polymorphic form of asenapine maleate is characterised by the XRPD spectrum shown in FIG. 6. The 2θ angles, the interplanar distance and the intensity of the peaks are shown in Table 2. The most intense peaks are those at 2θ values of 18.22°; 18.46°; 20.06°; 20.82°; 20.98°; 21.16°; and 21.66°.

Figure 9:
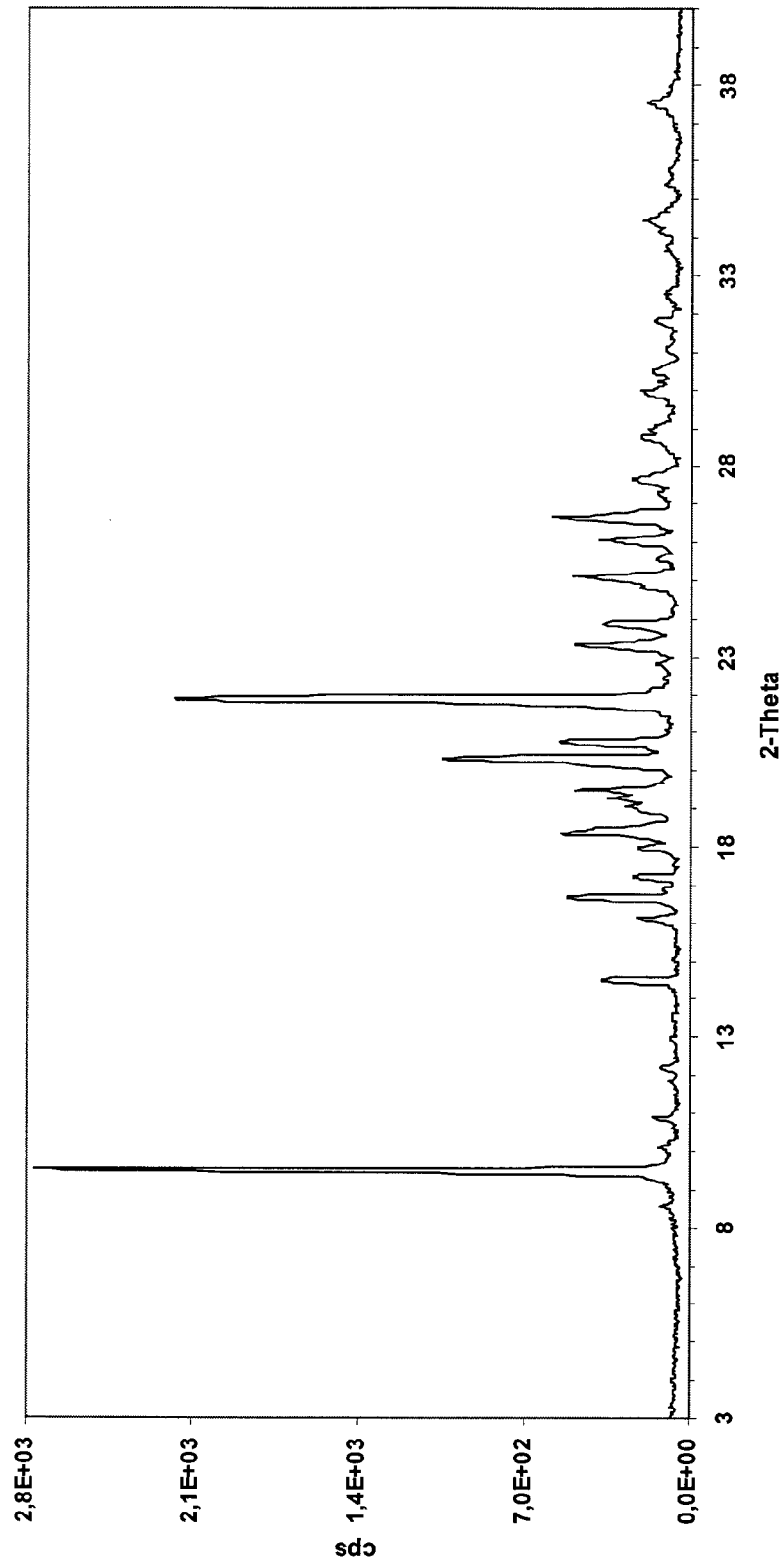
FIG. 9 shows the XRPD spectrum of the monoclinic form of asenapine maleate disclosed in U.S. Pat. No. 7,741,358.

The monoclinic form of asenapine maleate disclosed in U.S. Pat. No. 7,741,358 is characterised by an XRPD spectrum as shown in FIG. 9. The characteristic peaks are those at 2θ values of 9.6°; 20.4°; 22.0°; 23.4°; 25.2°; 26.1°; and 26.7°.

Figure 12:
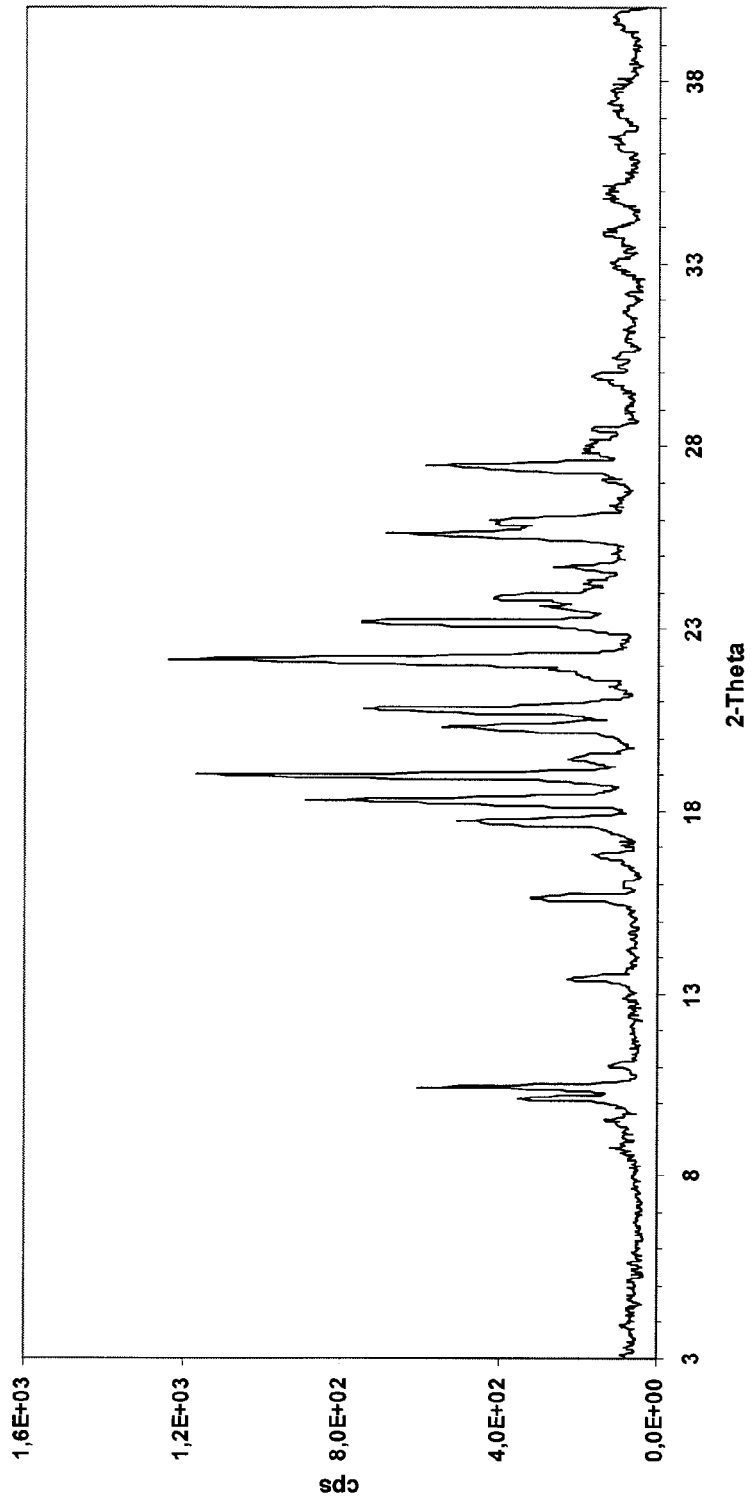
FIG. 12 shows the XRPD spectrum of the orthorhombic form of asenapine maleate disclosed in U.S. Pat. No. 7,741,358.

The orthorhombic form of asenapine maleate disclosed in U.S. Pat. No. 7,741,358 is characterised by an XRPD spectrum as shown in FIG. 12. The characteristic peaks are those at 2θ values of 10.5°; 15.7°; 18.3°; 19.0°; 20.3°; 20.8°; 22.2°; 23.2°; 25.6°; and 27.5°.

A 2θ value as indicated above typically signifies the specified value±0.2°.

TABLE 2

XRPD data for asenapine maleate

| 2-theta angle (°) | Interplanar distance d (Å) | Intensity (%) |
|---|---|---|
| 6.58 | 13.4222 | 10 |
| 9.04 | 9.7745 | 7 |
| 9.20 | 9.6048 | 9 |
| 9.44 | 9.3612 | 14 |
| 10.34 | 8.5483 | 6 |
| 12.06 | 7.3327 | 2 |
| 12.64 | 6.9975 | 2 |
| 13.18 | 6.7120 | 13 |
| 13.56 | 6.5248 | 3 |
| 14.62 | 6.0540 | 2 |
| 14.96 | 5.9172 | 7 |
| 15.68 | 5.6470 | 2 |
| 16.42 | 5.3942 | 4 |
| 16.74 | 5.2918 | 13 |
| 17.62 | 5.0294 | 5 |
| 18.22 | 4.8651 | 42 |
| 18.46 | 4.8024 | 100 |
| 19.00 | 4.6671 | 15 |
| 19.56 | 4.5348 | 8 |
| 20.06 | 4.4228 | 37 |
| 20.52 | 4.3247 | 21 |
| 20.82 | 4.2631 | 30 |
| 20.98 | 4.2309 | 36 |
| 21.16 | 4.1953 | 49 |
| 21.66 | 4.0996 | 37 |
| 22.00 | 4.0370 | 6 |
| 22.50 | 3.9484 | 12 |
| 23.10 | 3.8472 | 7 |
| 23.64 | 3.7605 | 6 |
| 24.30 | 3.6599 | 15 |
| 24.48 | 3.6334 | 15 |
| 25.04 | 3.5534 | 10 |
| 25.42 | 3.5011 | 18 |
| 25.64 | 3.4715 | 14 |
| 26.18 | 3.4012 | 5 |
| 26.50 | 3.3608 | 6 |
| 27.30 | 3.2641 | 10 |
| 27.86 | 3.1998 | 12 |
| 28.08 | 3.1752 | 6 |
| 28.62 | 3.1165 | 4 |
| 28.72 | 3.1059 | 5 |
| 28.94 | 3.0828 | 4 |
| 30.06 | 2.9704 | 5 |
| 30.70 | 2.9099 | 4 |
| 31.84 | 2.8083 | 5 |
| 32.36 | 2.7643 | 3 |
| 32.70 | 2.7364 | 3 |
| 32.98 | 2.7138 | 3 |
| 33.92 | 2.6407 | 5 |
| 33.98 | 2.6362 | 5 |

TABLE 2-continued

XRPD data for asenapine maleate

| 2-theta angle (°) | Interplanar distance d (Å) | Intensity (%) |
|---|---|---|
| 34.22 | 2.6182 | 6 |
| 34.66 | 2.5860 | 10 |
| 35.80 | 2.5062 | 7 |
| 38.52 | 2.3353 | 9 |
| 38.66 | 2.3271 | 14 |

The monoclinic structure of the novel monoclinic polymorphic form of asenapine maleate has been determined by X-ray powder diffraction spectrum, which shows the following unit cell:
Crystalline system: monoclinic
Spatial group: P21/c
a=18,732(2) Å
b=19,212(2) Å
c=11,378(1) Å
β=94.57°

The novel polymorphic monoclinic form of asenapine maleate according to the invention presents chemico-physical and biopharmaceutical properties such as stability, dissolution rate and bioavailability which make it advantageous for use in the preparation of pharmaceutical forms containing asenapine maleate.

A further object of the invention is therefore a pharmaceutical composition containing the novel monoclinic crystalline form of asenapine maleate according to the invention and a pharmaceutically acceptable excipient.

The invention will now be illustrated by the following examples.

EXAMPLES

The IR spectra were obtained with a Perkin Elmer Spectrum 1000 spectrometer, samples in KBr pellets, 16 scans, resolution 4 cm$^{-1}$.

The DSC thermograms were obtained with a Perkin Elmer Pyris 1 calorimeter, in nitrogen atmosphere, with temperature ramp from 40° C. to 160° C. at 5° C./min.

The XRPD diffraction spectra were obtained with an Ital-Structure θ/θ automatic diffractometer [CuKα radiation (λ=1.5418 Å); diffraction angle interval 3≤2θ≤40°; step amplitude 0.02°; step count time 5 sec; voltage 40 kV, current 30 mA] and expressed in terms of Bragg 2-theta angles (2θ), interplanar distances d and relative intensities (expressed as a percentage of the most intense diffraction peak).

Example 1

Synthesis of trans-5-chloro-2,3,3a,12b-tetrahydro-2-methyl-1H-dibenz[2,3:6,7]-oxepino[4.5-c]pyrrole (asenapine base)

Anhydrous tetrahydrofuran (10 L) is loaded into a reactor maintained under inert atmosphere, cooled to 0° C. and stirred, and aluminium chloride is added in aliquots (0.7 Kg). 3.5 L of a 10% solution of lithium aluminium hydride in tetrahydrofuran is added to the solution, maintaining it at a temperature of under 10° C. The solution is maintained at 0° C. for 15 minutes. A solution of trans-1'-chloro-2,3,3a,12b-tetrahydro-2-methyl-1H-dibenz[2,3:6,7]oxepino[4,5-c]pyrrol-1-one (1 Kg) in anhydrous tetrahydrofuran (10 L) is dripped into the solution, maintaining a temperature of under 15° C. The solution is stirred for 1 hour at 10° C. An 0.6 N solution of sodium hydroxide (10 L) is dripped slowly into the reaction mixture, maintaining the temperature at under 10° C. Toluene (15 L) and water (10 L) are added, and the solution is stirred for 15 minutes at 20° C. The lower aqueous phase is separated. Extraction from the aqueous phase is performed with toluene (2×50 L). The organic phases are combined, and the solvent is evaporated under vacuum to obtain asenapine base (0.9 Kg) in the form of oil. Purity=97% (HPLC).

Example 2

Synthesis of Asenapine Phosphate from Asenapine Base 0.71 Kg of crude asenapine base (2.48 moles) and 6.7 L of ethanol are loaded into a reactor and dissolved by heating at 50° C. An 85% solution of phosphoric acid (0.17 L, 2.48 moles) in ethanol (1.0 L) is dripped into the solution of asenapine base at 50° C. in 10 minutes. The solution is stirred for 30 minutes at 50° C. The solution is cooled to 25° C. in approx. 2 hours. The solution is left under stirring at 25° C. for 2 hours. The product is isolated by filtration, washing with ethanol (1.1 L). The product is dried under vacuum at 25° C. for 20 hours. 1 Kg of asenapine phosphate is obtained (yield=94.0%). Purity >99.5% (HPLC). The IR spectrum, the DSC thermogram and the XRPD spectrum of asenapine phosphate are shown in FIGS. 1, 2 and 3 respectively. Table 1 shows the Bragg 2-theta angles (2θ), interplanar distances d and the relative intensities expressed as a percentage of the most intense diffraction peak. Table 3 shows the improvement in the quality of the product, expressed as HPLC area %, obtained in the conversion from asenapine base to asenapine phosphate. In Table 3, RRT indicates the relative retention time of the impurities present in the product obtained, compared with the retention time of asenapine.

TABLE 3

Variation in quality from asenapine base to asenapine phosphate

| Product | Asenapine (Area %) | RRT 0.7 (Area %) | RRT 0.8 (Area %) | RRT 0.9 (Area %) | RRT 0.95 (Area %) | RRT 2.8 (Area %) | RRT 3.3 (Area %) |
|---|---|---|---|---|---|---|---|
| Asenapine base | 96.9 | 0.05 | 0.12 | 1.77 | 0.30 | 0.15 | 0.48 |
| Asenapine phosphate | 99.8 | 0.00 | 0.06 | 0.00 | 0.14 | 0.00 | 0.00 |

Example 3

Purification of Asenapine Maleate by Isolating Asenapine Phosphate 0.69 Kg of asenapine maleate (1.69 moles) with a purity of 98% (HPLC) is loaded into a reactor. Toluene (7.2 L) is added, and the suspension is stirred at 25° C. A 9% solution of sodium bicarbonate (7.2 L) is added by dripping. The solution is left under stirring at 25° C. for 30 minutes. The lower aqueous phase is eliminated. The organic phase is washed with water (2×3.6 L). The solvent is evaporated under vacuum, obtaining asenapine base (0.50 Kg) in the form of oil. 4.6 L of ethanol is added. The solution is stirred, heating to 50° C. An 85% solution of phosphoric acid (0.12

L, 1.69 moles) in ethanol (0.68 L) is dripped into the solution of asenapine base at 50° C. in 10 minutes. The solution is stirred for 30 minutes at 50° C. The solution is cooled to 25° C. in approx. 2 hours. The solution is left under stirring at 25° C. for 2 hours. The product is isolated by filtration, washing with ethanol (0.75 L). The product is dried under vacuum at 25° C. for 20 hours. 0.614 Kg of asenapine phosphate is obtained (yield=94.0%). Purity >99.5% (HPLC).

Example 4

Synthesis of Asenapine Maleate from Asenapine Phosphate 1.38 Kg of asenapine phosphate is loaded into a reactor. Toluene (15 L) is added, and the suspension is placed under stirring. A 9% solution of sodium bicarbonate (15 L) is added by dripping. The solution is left under stirring at 25° C. for 30 minutes. The lower aqueous phase is eliminated. The organic phase is washed with water (2×7 L). The solvent is evaporated under vacuum, obtaining asenapine base (0.90 Kg) in the form of oil. Isopropanol (12 L) is loaded into the reactor and dissolved by heating at 50° C. Maleic acid (0.4 Kg) is added to the asenapine base solution at 50° C. The solution is cooled to 25° C. in approx. 2 hours. The solution is left under stirring at 25° C. for 2 hours. The product is isolated by filtration, washing with isopropanol (3 L). The product is dried under vacuum at 50° C. for 20 hours. 1 Kg of asenapine maleate is obtained.

The IR spectrum, DSC thermogram and XRPD spectrum of the novel monoclinic form of asenapine maleate thus obtained are shown in FIGS. 4, 5 and 6 respectively. Table 2 shows the Bragg 2-theta angles (2θ), interplanar distances d and the relative intensities expressed as a percentage of the most intense diffraction peak.

Figure 8:
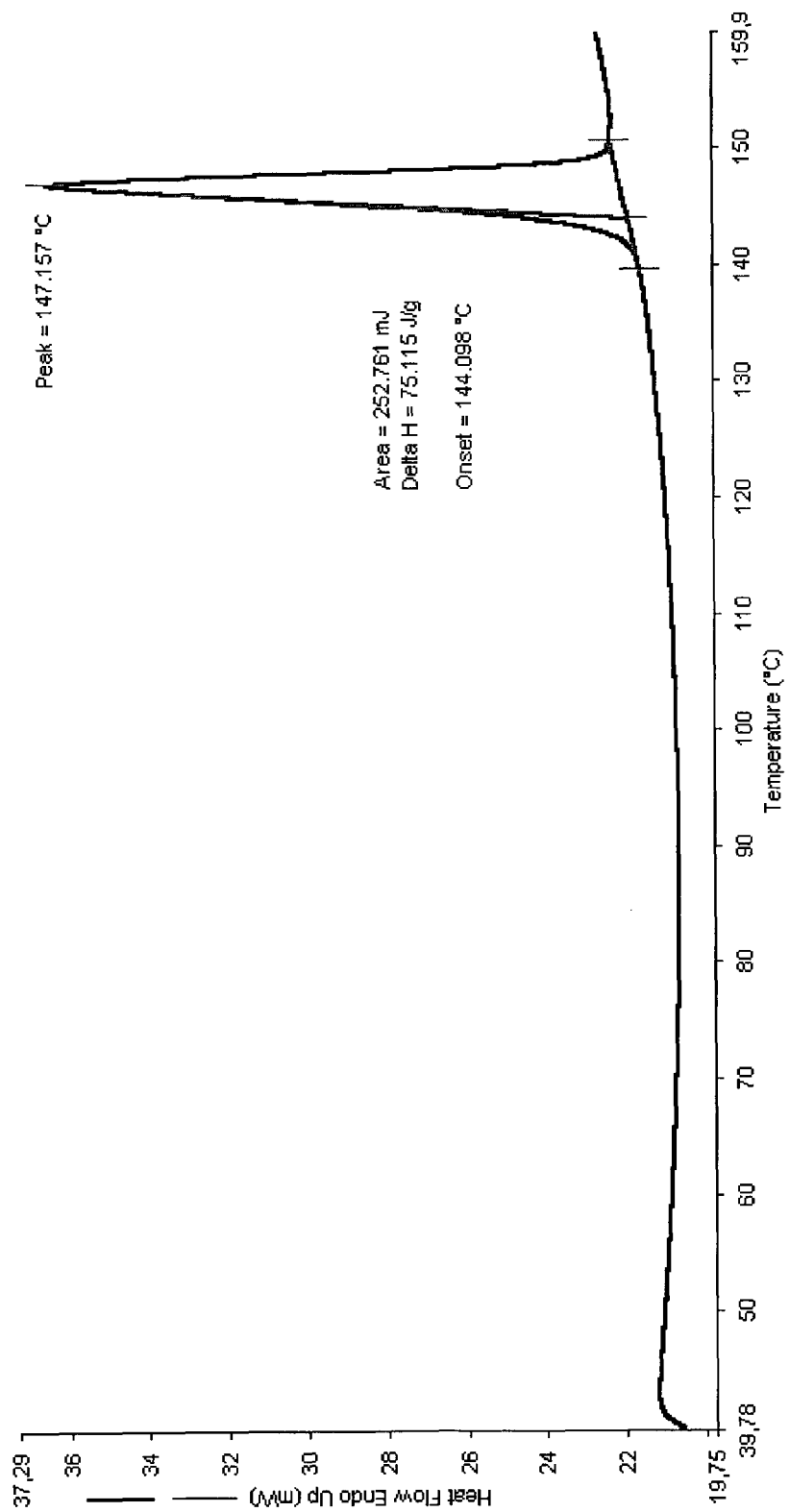
FIG. 8 shows the DSC thermogram of the monoclinic form of asenapine maleate disclosed in U.S. Pat. No. 7,741,358.

FIGS. 7, 8 and 9 show the IR spectrum, DSC thermogram and XRPD spectrum respectively of the monoclinic form disclosed in U.S. Pat. No. 7,741,358.

Figure 11:
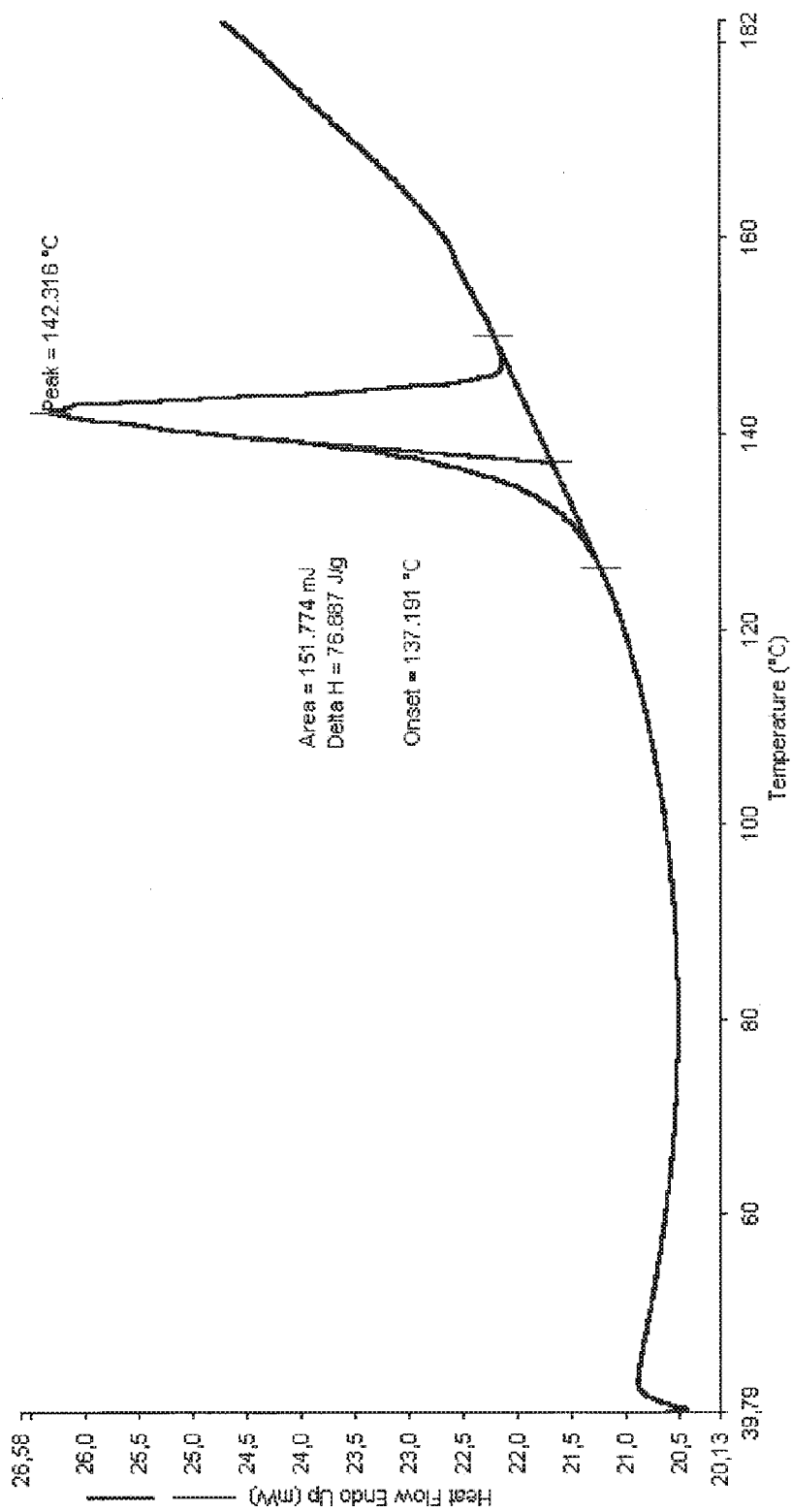
FIG. 11 shown the thermogram of the orthorhombic form of asenapine maleate described in U.S. Pat. No. 7,741,358.

FIGS. 10, 11 and 12 show the IR spectrum, DSC thermogram and XRPD spectrum respectively of the orthorhombic form disclosed in U.S. Pat. No. 7,741,358.

Figure 13:
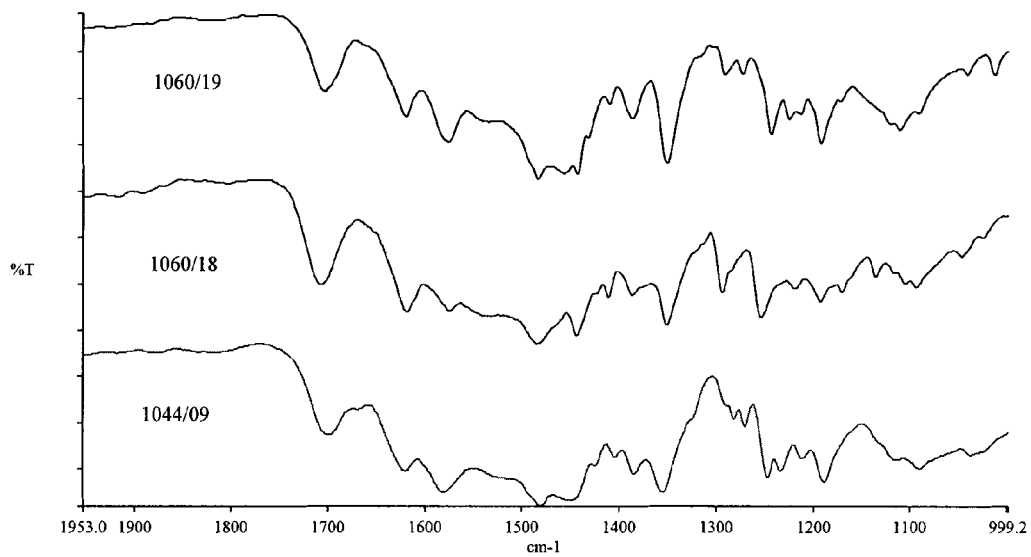
FIG. 13 shows the superimposition of the IR spectra of the novel monoclinic form of asenapine maleate, the monoclinic form disclosed in U.S. Pat. No. 7,741,358 and the orthorhombic form disclosed in U.S. Pat. No. 7,741,358.
Figure 13:
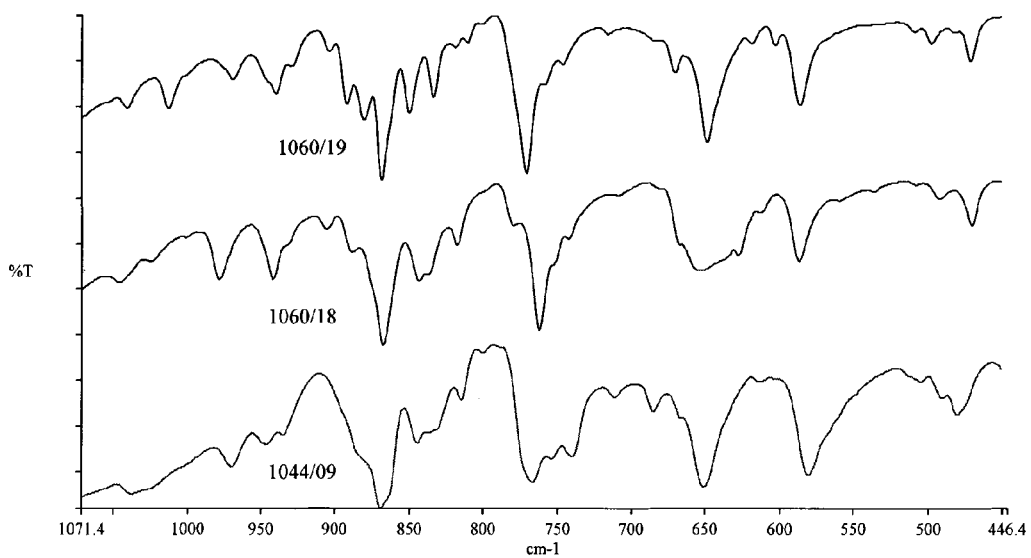
Figure 14:
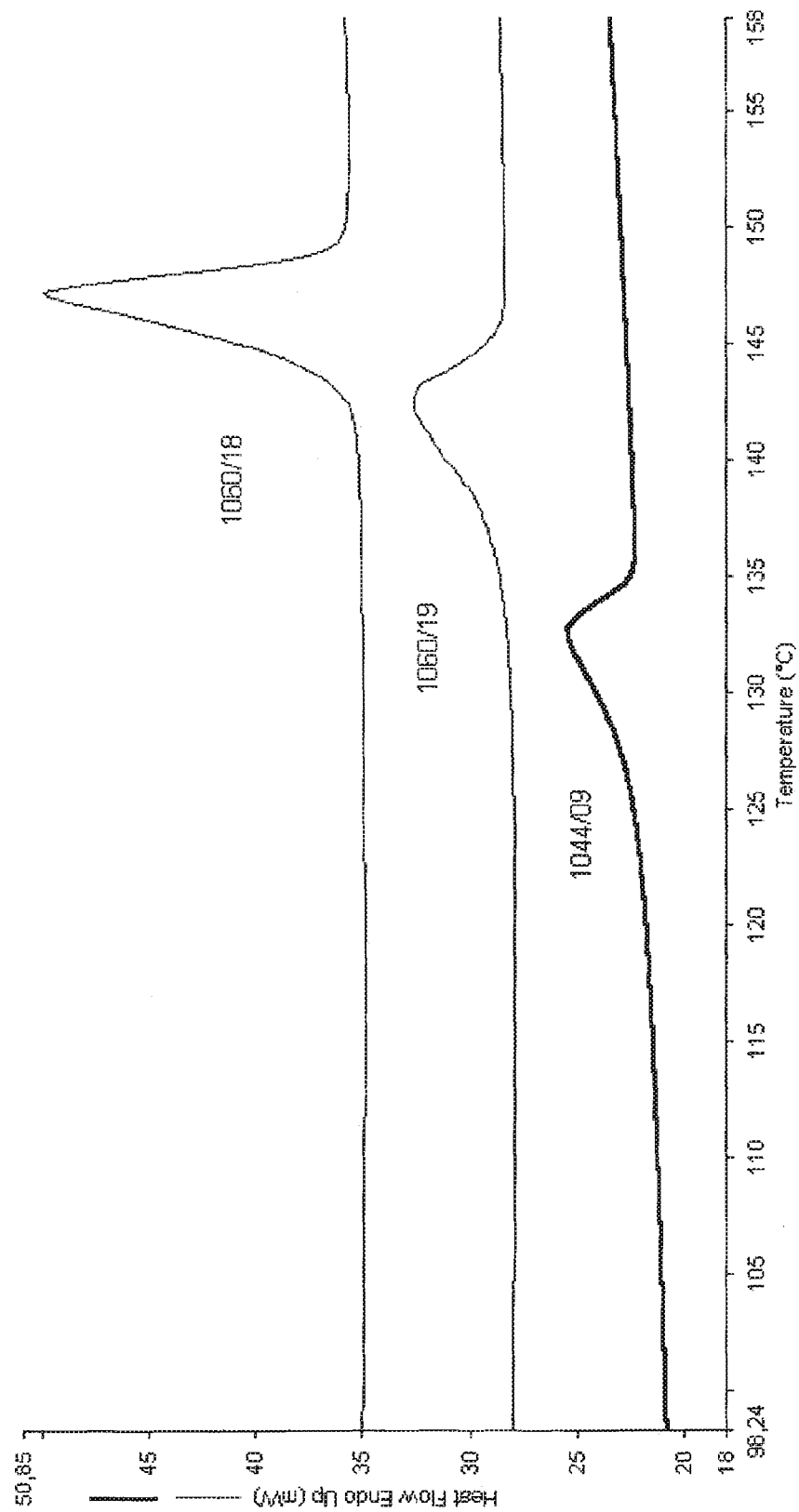
FIG. 14 shows the superimposition of the DSC thermograms of the novel monoclinic form of asenapine maleate, the monoclinic form disclosed in U.S. Pat. No. 7,741,358 and the orthorhombic form disclosed in U.S. Pat. No. 7,741,358.

The superimposition of the IR spectra and the DSC thermograms of the novel monoclinic form of asenapine maleate (sample 1044/09), the monoclinic form disclosed in U.S. Pat. No. 7,741,358 (sample 1060/18) and the orthorhombic form disclosed in U.S. Pat. No. 7,741,358 (sample 1060/19) are shown in FIGS. 13 and 14 respectively.

The invention claimed is:
1. Asenapine phosphate of formula (I), or its enantiomer

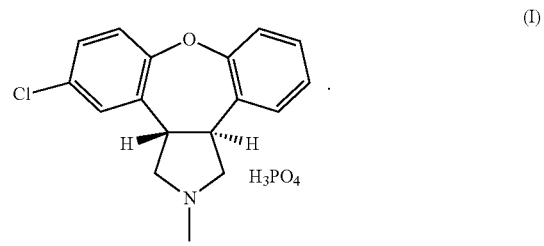

2. Asenapine phosphate of claim 1, in the crystalline form.
3. Asenapine phosphate as claimed in claim 2, characterised by an XRPD spectrum (CuKα radiation λ=1.5418 Å) having peaks at 2θ values of 12.32°; 14.14°; 14.82°; 15.10°; 15.54°; 18.66°; 22.44°; and 24.10; and wherein said 2θ values mean the specified value±0.2°.
4. Asenapine phosphate as claimed in claim 2, characterised by an XRPD spectrum (CuKα radiation λ=1.5418 Å) having the 2θ angles, interplanar distances and peak intensities reported in Table 1.
5. Process for the preparation of asenapine phosphate of claim 2, comprising reacting asenapine base with phosphoric acid in an organic solvent.
6. A process as claimed in claim 5, wherein asenapine base is obtained by neutralising an asenapine salt with a base.
7. A process as claimed in claim 5, wherein 1 to 2 moles of phosphoric acid are used per mole of asenapine.
8. Process as claimed in claim 5, wherein the organic solvent is selected from acetone, methyl ethyl ketone, methyl iso-butylketone, cyclohexanone, ethyl acetate, butyl acetate, isopropyl acetate, dimethyl carbonate, tetrahydrofuran, methyl tetrahydrofuran, ter-butyl methyl ether, ethyl ether, di-isopropyl ether, diethoxymethane, ethylene glycol dimethyl ether, toluene, xylene, chlorobenzene, methylene chloride, chlorobutane, methanol, ethanol, isopropanol, n-propanol, or mixtures thereof, and wherein said solvents can contain percentages of water up to 10%.
9. Process as claimed in claim 5, wherein the organic solvent is selected from ethanol, aqueous ethanol or isopropanol.

* * * * *